United States Patent [19]

Furutani et al.

[11] 4,160,646
[45] Jul. 10, 1979

[54] METHOD OF ANALYZING LIQUID SAMPLES AND SYSTEM FOR CONTINUOUSLY AUTOMATICALLY ANALYZING SAME

[75] Inventors: Yoshikazu Furutani; Shinichi Kishimoto, both of Kyoto, Japan

[73] Assignee: Kabushiki Kaisha Kyoto Daiichi Kagaku, Kyoto, Japan

[21] Appl. No.: 853,137

[22] Filed: Nov. 21, 1977

[30] Foreign Application Priority Data

Jan. 20, 1977 [JP] Japan ................................ 52-5508

[51] Int. Cl.² .................. G01N 21/30; G01N 21/48; G01N 31/22; G01N 33/16
[52] U.S. Cl. ................................ 23/230 R; 23/230 B; 356/448; 422/56
[58] Field of Search .......... 23/253 R, 253 TP, 230 R; 356/212; 256/199, 209

[56] References Cited

U.S. PATENT DOCUMENTS

| 3,232,710 | 2/1966 | Rieckmann et al. | 23/253 TP |
| 3,907,503 | 9/1975 | Betts et al. | 23/253 TP |
| 3,918,910 | 11/1975 | Soya | 23/253 R |
| 3,932,132 | 1/1976 | Hijikata | 23/253 R |
| 3,932,133 | 1/1976 | Ishikawa | 23/253 TP |
| 3,980,437 | 9/1976 | Kishimoto et al. | 23/253 TP |

Primary Examiner—R. E. Serwin
Attorney, Agent, or Firm—Darby & Darby

[57] ABSTRACT

A method of analyzing a liquid sample by applying the sample to a composite test paper composed of a strip plastic transparent film and a reflectivity reference or compensation paper piece and a plurality of color reaction test paper pieces affixed to the strip, feeding the test paper to a spectral reflectivity measuring device a predetermined period of time after the application, and calculating the corrected reflectivities of each of the paper pieces from the measured amounts of reflected light at varying wavelengths to determine the concentration of the abnormal substance contained in the test sample, free of measuring errors due to the color if any of the sample, differences in the color developed and variations in the thickness of the color reaction test paper pieces and reflectivity reference or compensation paper piece. A system for practicing this method is also disclosed.

16 Claims, 12 Drawing Figures

METHOD OF ANALYZING LIQUID SAMPLES AND SYSTEM FOR CONTINUOUSLY AUTOMATICALLY ANALYZING SAME

RELATED APPLICATION

In U.S. patent application Ser. No. 668,745, which is assigned to the assignee of the subject application, a method and system is described in which a reflectivity correcting paper piece and a test paper piece are dipped in a liquid sample to be tested to compensate for the measuring error resulting from the inherent color of the sample. The present invention relates to an improvement over the aforesaid application.

This invention relates to a method and a system for analyzing liquid samples such as the urine by determining the degree of color development on chemical color reaction test paper pieces in terms of spectral reflectivity, and more particularly to a method of analysis in which fluctuations or errors involved in the reflectivity due to the color of the test sample itself or variations in the thickness or reflectivity characteristics of color reaction test paper pieces are compensated for or reduced by the use of several measuring wavelengths and also to a system for continuously automatically practicing this method.

For convenience sake, chemical color reaction test papers have heretofore been used widely for urine analysis or for the measurement of pH or the like of waste water, river water and other aqueous solutions. It is fair to say that urine analysis, in particular, is conducted predominantly with the use of color reaction test papers including those of the composite type which are adapted to check the sample by a single procedure for pH and for the presence of a wide variety of substances such as glucose, proteins, occult blood, ketones and bilirubin. In fact, such color reaction test papers are extensively used for the measurement of pH values and for the detection of abnormal substances.

The use of color reaction test papers may be justifiable because they are easy to use and because the determination of whether an abnormal substance is present or absent is generally of importance. However, the color reaction on the test paper is unstable since the reaction proceeds with time and involves discoloration soon after saturation is reached. Moreover, the color if any of the urine per se will affect the color development, while the comparison between a color standard and the color developed on the test paper, usually conducted with the unaided eye, does not indicate the amount of abnormal substance contained, possibly failing to accurately reveal even the presence or absence of such substance. Thus the color reaction test papers are of low reliability.

Accordingly, a method as well as a system therefor has been proposed in recent years in which the color produced on the test paper is measured, a specified period of time after the application of the test sample to the paper, in terms of spectral reflectivity with use of an efficient optical device in place of the unaided eye. FIG. 1 shows a composite test paper 1 used in the proposed method. In this method this paper is adapted not only for the detection of abnormal substances in the urine but also for more quantitative analysis of such substances and permits a prompt and efficient examination.

Stated more specifically, the test paper 1 comprises a strip of plastic or like material 2 and color reaction test paper pieces 3a, 3b, 3c, ... affixed to the stick 2 and each reactive with glucose, protein or like substance in the urine to produce a color with an intensity in accordance with the concentration of the substance like conventional composite-type test papers. The paper 1 further includes a reflectivity reference or compensation paper piece 4 affixed to one end of the strip 2. The portions 5 of the strip 2 on which the paper pieces are affixed may be colored black to block the transmitting light.

Each of the test paper pieces 3a, 3b, 3c, ... is prepared as by impregnating filter paper with a reagent to a constant density all over the filter paper which reagent will produce a color on selective reaction with glucose or the like. A piece of the same filter paper as used as the base material for the test paper pieces is used as the reflectivity reference or compensation paper piece 4.

For examination a urine sample is applied to the test paper pieces 4, 3a, 3b, 3c, ... or the paper pieces are immersed in the sample, and the reflectivities of the test paper pieces are measured. The reflectivities of the pieces 3a, 3b, 3c are converted to values relative to the reflectivity of the reflectivity reference or compensation paper piece 4 which is assumed to be 100% and are thereby corrected, whereby the influence of the color of the urine sample on the reflectivities can be eliminated. Thus, the reflectivity reference or compensation paper piece 4 serves the same purpose as the sample blank in colorimetric analysis.

FIG. 2 substantiating the above correction shows reflectivities of the color reaction test paper pieces 3 relative to the reflectivity, assumed to be 100%, of the reflectivity reference or compensation paper piece 4 to which water is applied. Curve A represents the reflectivity in the case of a colorless urine sample containing an abnormal substance, Curve B with a colored urine sample containing no abnormal sustance and Curve C with a colored urine sample containing an abnormal substance. When the test piece is observed with the unaided eye, the reaction spectrum represented by Curve C will be observed as a whole, and it is by no means possible to observe the degree of color development as normalized. On the other hand, the reflectivity characteristics curve resulting from the correction according to the foregoing method is approximately equivalent to Curve A, so that the abnormal substance is determinable with high precision independently of the color of the urnine sample.

This will be apparent from the results of an experiment shown in FIG. 3. Simulated samples were prepared from a colorless urine containing a specific abnormal substance with addition of a dye in varying concentrations and were applied to reflectivity reference or compensation paper pieces 4. The relative reflectivities $R_1$ of the pieces 4 were determined based on the reflectivity of a reflectivity reference or compensation paper piece 4 to which pure water was applied which reflectivity was assumed to be 100%. The relative reflectivities $R_1$ are plotted on the abscissa vs. corrected reflectivities $R_2$ on the ordinate. The corrected reflectivities $R_2$ were obtained by applying the simulated samples to reflectivity reference or compensation paper pieces 4 and color reaction test paper pieces 3 for detecting the specific abnormal substance and measuring the reflectivities of the pieces 4 and 3.

FIG. 3 reveals that even when the reflectivity reference or compensation paper piece 4 decreases in reflectivity by about 30%, the relative reflectivity of the color reaction test paper piece 3 remains almost unchanged.

However, the use of the foregoing method and system still involves the following problems, which make it difficult to accurately determine the concentrations of abnormal substances.

(1) The color reaction test paper pieces 3a, 3b, 3c, . . . have varying spectral reflectivity characteristics; at a certain measuring wavelength, one test piece may undergo a great variation in reflectivity, whereas another test piece will exhibit a small variation in reflectivity. In such an instance, difficulty will be encountered with the use of the test piece of small variation in accurately determining the reflectivity or the concentration of abnormal substance.

(2) When an integrating sphere is used for accurate measurement of the amount of reflected light, alterations in the distance between the reflecting surface and the integrating sphere will produce marked variations in the amount of reflected light. If a difference in thickness occurs between the reflectivity reference or compensation paper piece 4 and the color reaction test paper pieces 3a, 3b, 3c, . . . upon absorption of the urine sample, a difference will be produced in the distance between the integrating sphere and the reflecting surfaces, giving rise to an error in the corrected reflectivity.

The drawbacks of the conventional method or system arise solely from the use of a single wavelength for the measurement of the reflectivity. This appears to indicate that the above problems can be overcome by the use of several appropriate wavelengths for the measurement.

The object of this invention is to overcome the above problems by the use of a simple system by which reflectivities of color reaction test paper pieces are measured with the use of several kinds of rays having specified wavelengths, and an optimum corrected reflectivity is calculated for each paper piece. In the case where the variation in the amount of reflected light due to a variation in concentration is great at a specific wavelength, the corrected reflectivity at this wavelength is divided by the corrected reflectivity at another wavelength involving a small variation, and the resulting quotient is taken as the corrected reflectivity of the test paper piece concerned.

This invention will be described below in detail with reference to the accompanying drawings, in which.

First, the structure and the main functions of the analyzing system of this invention will be described briefly.

The analyzing system according to this invention consists mainly of a reflectivity measuring unit, a sample feeding unit, a wavelength selector and a data processing unit. The sample feeding unit comprises a rotary sample table in the form of a disk having radial grooves for receiving sheets of composite test paper in position, drive means for intermittently rotating the sample table and scanning means for the test paper, whereby the test paper to which a test sample is applied is conveyed from a specified position to the detecting portion of the reflectivity measuring unit and is sent out after measurement. The reflectivity measuring unit projects the measuring light from the wavelength selector onto the test paper, measures the light reflected from the surface of the paper and feeds the resulting signal to the data processing unit. The data processing unit receives various signals to perform operation, memory and control and gives output signals, for example, indicating the concentration of component to show the results of examination in operative relation to a printer or the like.

Figure 2:
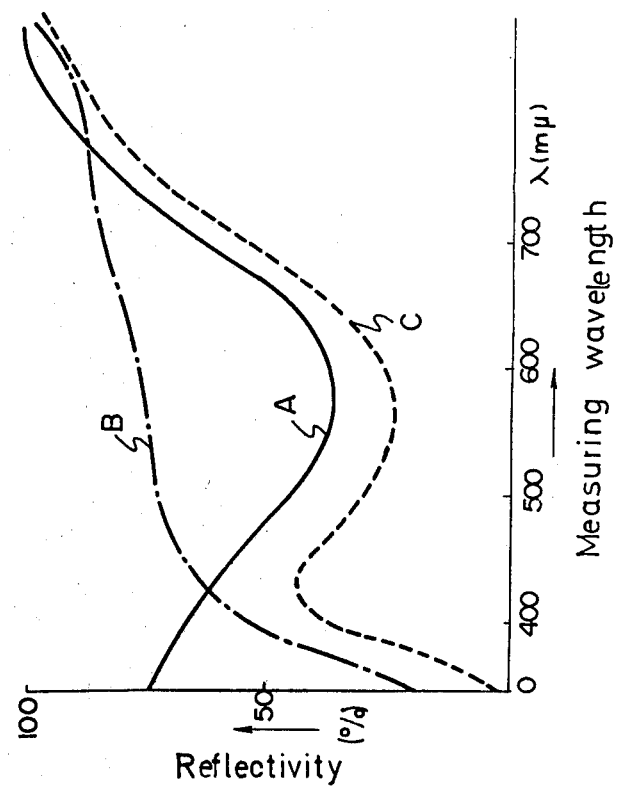
FIG. 2 is a diagram showing curves representing the spectral reflectivity characteristics of a color reaction test paper piece.
Figure 1:
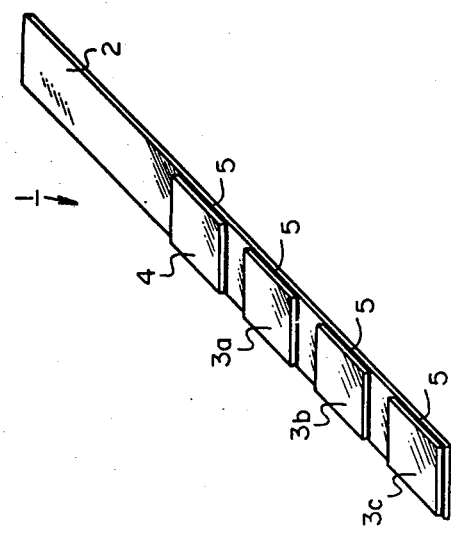
FIG. 1 is a perspective view showing an example of composite test papers useful in this invention.
Figure 4:
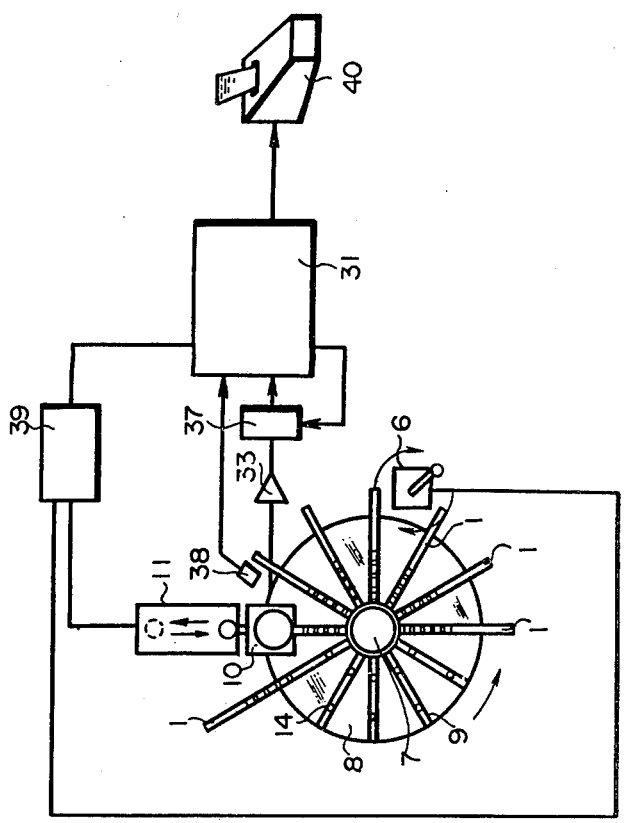
FIG. 4 is a block diagram showing an analyzing system according to this invention in its entirety with part omitted.
Figure 3:
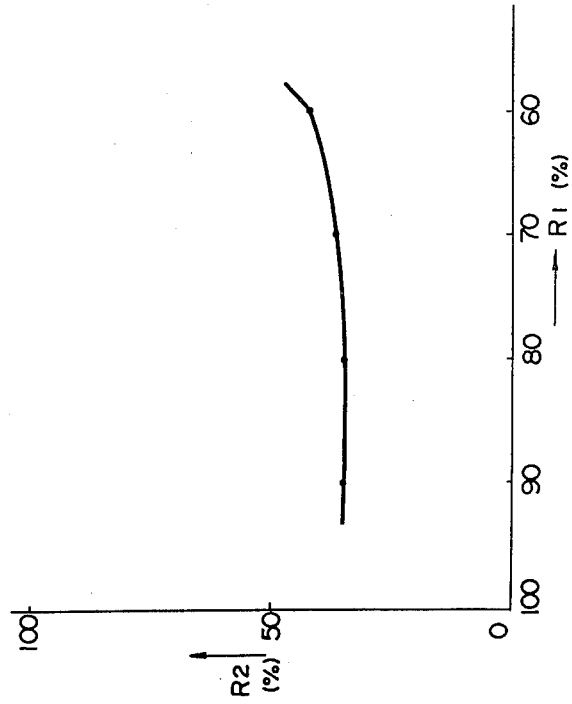
FIG. 3 is a diagram showing the relative reflectivity of a color reaction test paper piece determined with use of a reflectivity reference or compensation paper piece.
Figure 5:
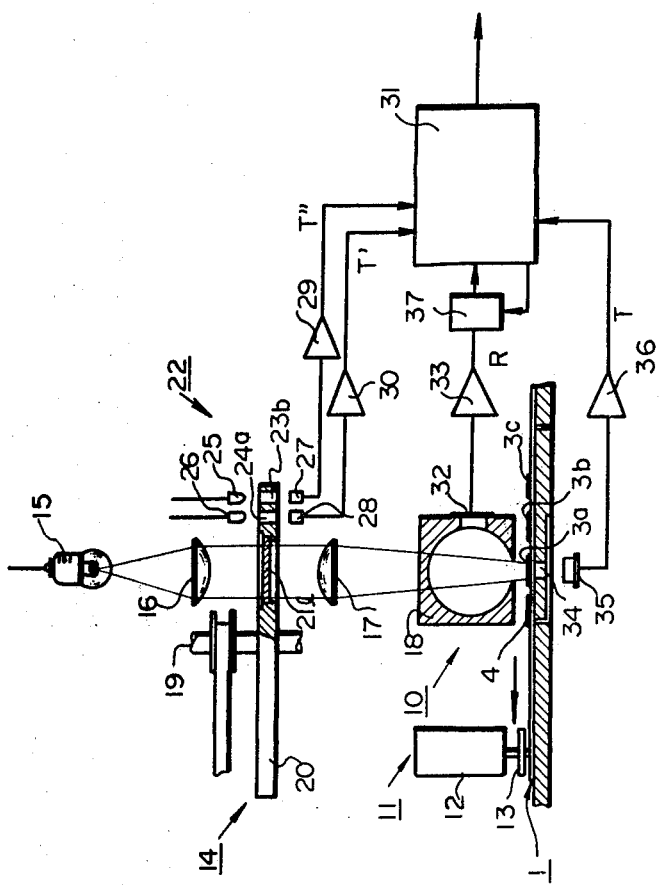
FIG. 5 is a schematic side elevation showing the main part of the analyzing system.

This invention will be described below in detail with reference to a preferred embodiment. FIG. 4 is a schematic block diagram showing the analyzing system of this invention in its entirety, and FIG. 5 is a schematic side elevation showing the main part of the same. A composite test paper 1 to which a test sample is applied is placed by a feeder 6 into one of grooves 9 formed radially in the front surface of a rotary sample table 8 and suitably spaced, for example at an angular spacing of 30°. The sample table 8 is intermittently rotated in the direction of the arrow about a shaft 7. After a definite period of time, the test paper 1 is brought to a position immediately below a reflectivity measuring unit 10 disposed above the path of travel of a peripheral portion of the table 8 and is held stopped for a given period of time. The duration of the rotation of the sample table 8 and the duration of the stop thereof can be determined as desired; for example, if the table is rotated for 2 seconds at a time and subsequently stopped for 8 seconds, a turn of its rotation will take 2 minutes. Thus if the test paper 1 is fed to the table 8 at a definite position, the reflectivity can be measured at a definite period of time after the application of the test sample to the paper.

While the sample table 8 is stopped, a scanning means 11 moves the test paper 1 along the groove 9 horizontally outward at a constant speed. The scanning means 11 comprises for example a horizontally reciprocally movable solenoid 12 which projects a movable spike 13 with specified timing to move the test paper 1, whereby the reflectivity reference or compensation paper pieces 4 and color reaction test paper pieces 3a, 3b, 3c, . . . are successively passed immediately below the detecting portion of the reflectivity measuring unit 10 at a definite speed. The reflectivities of the paper pieces 4, 3a, 3b, 3c, . . . are measured during the passage, and the paper is thereafter moved further outward and removed from the sample table 8.

The reflectivities of the test paper 1 are measured in the following manner by the measuring unit 10 and a measuring wavelength selector 14 provided thereabove.

The rays from a light source lamp 15 are first made parallel by a collimator lens 16 and then directed to the wavelength selector 14, by which the rays of several specified wavelengths are selected. The selected rays pass through a condenser 17 and an integrating sphere 18 and impinge on the test paper 1 substantially perpendicular thereto.

Figure 6:
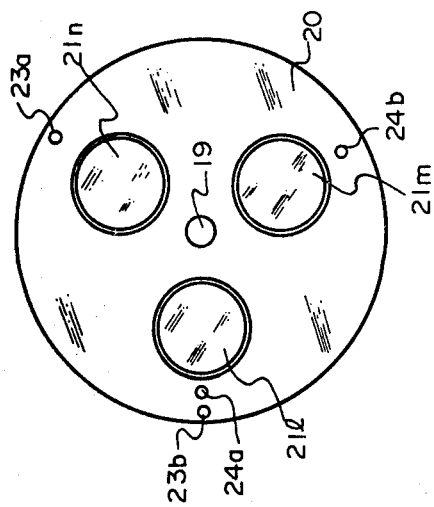
FIG. 6 is a plane view of a filter holder.

As shown in FIGS. 5 and 6, the wavelength selector 14 comprises a filter holder 10 rotatable at a high speed about a pin 19 and optical filters 21*l*, 21*m* and 21*n* corresponding in number to the number of the required wavelengths (i.e. three in this embodiment) and fitting in the filter holder 20 as arranged equidistantly, the filters being positionable concentrically with the optical axis. With the rotation of the filter holder 20, therefore, one of the filters is positionable in the light path in the order of: 21*l*→21*m*→21*n*, with the result that the wavelength of the rays irradiating the test paper 1 varies from l to m and further to n, if it is assumed that the filters transmit rays predominantly of wavelengths of l, m and n respectively.

A wavelength identifying signal generator 22 gives a timed signal for identifying the wavelength of the rays irradiating the test paper 1. As illustrated, the filter holder 20 is formed with small holes 23*b*, 24*a*, 24*b* and 23*a* positioned outward of the filters 21*l*, 21*m* and 21*n* fitting in the holder. When the holder is so positioned that the center of each of the filters is in alignment with the optical axis, light sources 25, 26 and light detectors 27, 28 are arranged above and below the holes, such that the signals from the light detectors 27 and 28 are fed to a data processing unit 31 by way of amplifiers 29 and 30 respectively.

Figure 7:
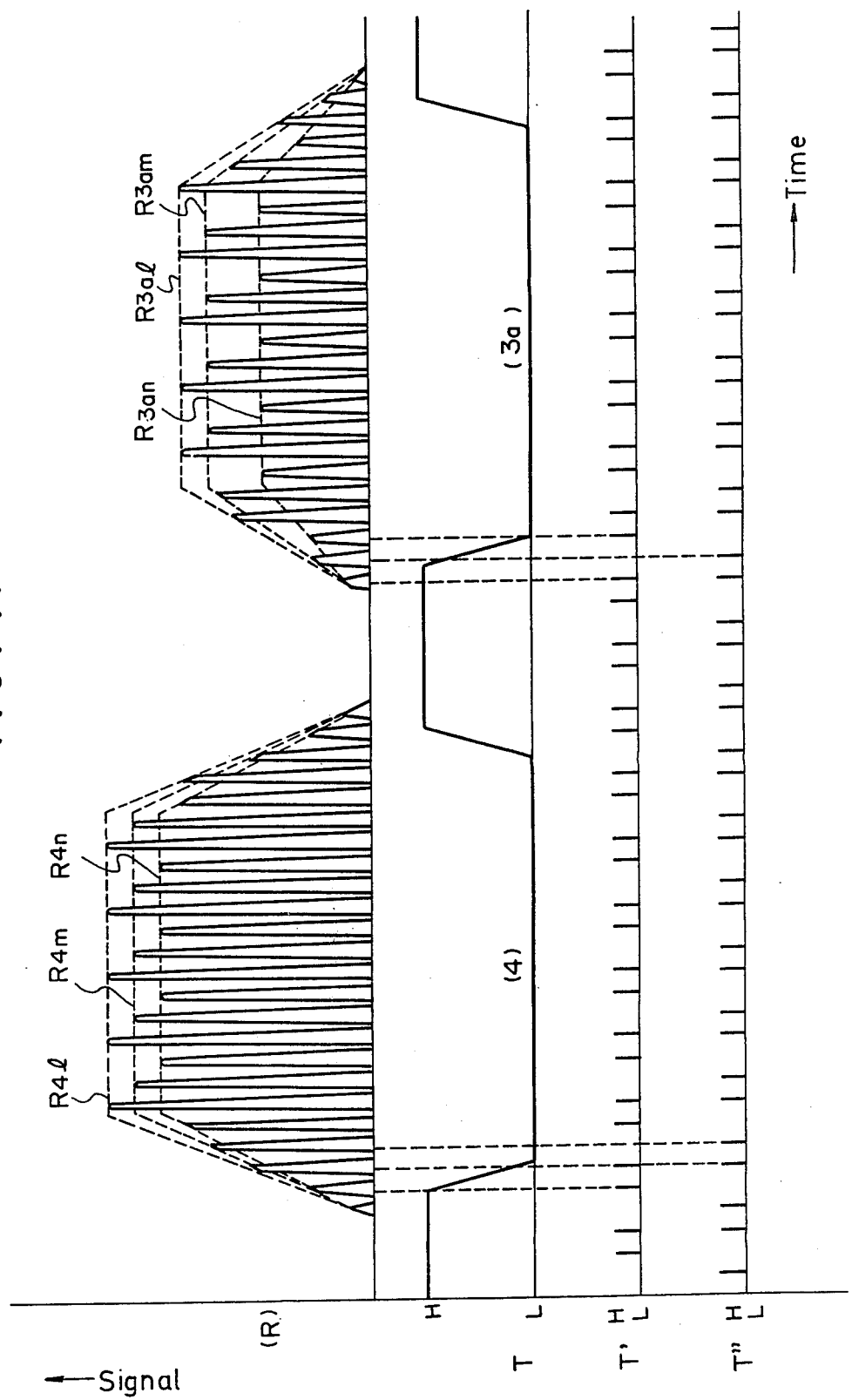
FIG. 7 is a diagram showing the timing relationship between the signals fed to a data processing unit.

It is now assumed that the amplifier 30 produces a signal T' when the light from the light source 26 reaches the light detector 28 and that the amplifier 29 produces a signal T" when the light from the light source 25 reaches the light detector 27. The rays irradiating the test paper 1 are those of wavelength of m passing through the filter 21*m* when T' is high (hereinafter abbreviated as "H") and T" is low (hereinafter abbreviated as "L"), are those of wavelength of n passing through the filter 21*n* when T" is H and T' is L, and are those having a wavelength of l and passing through the filter 21*l* when T' and T" are both H. FIG. 7 shows the timing relationship between the signals T' and T" and other signals.

The rays impinging on the test paper 1 substantially perpendicular thereto are reflected in the direction of $2\pi$ from the surface of the correcting paper piece 4 or of each of the test paper pieces 3*a*, 3*b*, 3*c*, . . . , and the measuring unit 10 measures the reflectivity at each wavelength for each of the paper pieces 4, 3*a*, 3*b*, 3*c* . . . . The measuring unit 10 comprises, for example, the integrating sphere 18, a light detector 32 and an amplifier 33 and produces signals R. On the other hand, the groove 9 of the sample table 8 is provided with an aperture 34 for passing the light passing through the test paper 1. The light impinges on the light detector 35, giving a signal T which is amplified by the amplifier 36 and then fed to the data processing unit 31.

The data processing unit 31 is a program memory electronic computer for performing calculation, storage and control. It has a plurality of input/output ports for giving and receiving digital signals. Data can be fed to and sent out from the unit 31 only through I/O ports selected by a program. The input ports of the data processing unit 31 receives the signal T" from the light detector 27, signal T' from the light detector 28, signal T from the light detector 35, output from an analogue-digital converter 37 and signal from a test paper sensor 38 shown in FIG. 4. The output signals from the output ports are a signal for starting the operation of the analogue-digital converter 37, a scanning initiating signal to a sequence controller 39 controlling the scanning means 11 and signals to a printer 40.

The embodiment described above operates in the following manner. In response to a signal from the test paper sensor 38 indicating that a test paper 1 has passed the position of the sensor 38, the data processing unit 31 erases all the measurement data stored in its memory and, upon lapse of a period of time (required for the test paper 1 to travel from the position of the sensor 38 to the detecting portion of the measuring unit 10 and to come to a halt), instructs the sequency controller 39 to actuate the scanning means 11.

Accordingly after that period of time, the scanning means 11 functions, slidingly moving the test paper 1 in the direction of the arrow in FIG. 5. At this time, the rays of wavelengths l, m and n irradiating the paper 1 are reflected when the paper pieces 4, 3*a*, 3*b* and 3*c* are positioned in the light path and impinge on the light detector 32 on the integrating sphere 18, producing signals R proportional to the amounts of reflected light. On the other hand, the rays through the test paper 1 strike the light detector 35, which in turn emits signals indicating the position of the test paper pieces 3*a*, 3*b*, 3*c*, . . . The signals R from the light detector 32 of the integrating sphere are amplified by the amplifier 33, while the signals T from the light detector 35 are amplified by the amplifier 36 which has a function to level off the signals. FIG. 7 shows the wave form of signals R from the light detector 32 on passing through the amplifier 33 and that of signals T from the light detector 35 on passing through the amplifier 36.

The signals T and R shown in FIG. 7 are those obtained with the use of a composite test paper 1 including a transparent strip 2. Accordingly the signals T representing the amounts of transmitted light are H at transparent portions and L at the portions of the paper pieces 4 and 3, whereas the signals R representing the amounts of reflected light are L at the transparent portions and H at the paper piece portions. Since the light is projected intermittently, the light reflected from the paper piece portions are represented by pulse signals.

However, the signals T, if pulsating, would function adversely because the data processing unit 31 starts to receive signals R upon detecting the alteration of signal T from H to L. The amplifier 36 therefore has a levelling-off function.

For the data processing unit 31 to have an access time from the moment the signal T varies from H to L to the moment the signals R representing amounts of the reflected light stabilize, the unit 31 counts the condition several times (e.g. two times in the case of signals R in FIG. 7) in which the timed signals T' and T" both become H.

Subsequently at the moments when T' is H and T" is L, when T" is H and T' is L and when T' and T" are both H, the unit 31 actuates the analogue-digital converter 37, which converts the signal R at each of the moments to a digital signal. The converted data indicating the amount of reflected light at a wavelength m when T' is H and T" is L is added to the contents of a memory $M_1$ (not shown) within the data processing unit 31. Similarly the converted data of the amount of reflected light at a wavelength n when T" is H and T' is L is stored in a memory $M_2$, and the converted data of the amount of reflected light at a wavelength l when both T' and T" are H is stored in $M_3$.

The series of operations from the moment when T' is H and T" is L to the moment when T' and T" are both H are repeated several times (e.g. five times in the wave form of FIG. 7) at the horizontal peak of signals R defined by a group of pulses representing the amounts of reflected light. The number of times of repetition is dependent on the number of revolutions of the filter holder 20, the speed of travel of the scanning means and the size of the paper pieces 4, 3a, 3b, 3c, . . . The greater the number of times of repetition, the greater is the number of reflectivity measuring positions on the paper piece and the more accurate are the values obtained.

Upon completion of the operations in a predetermined number of series, the data processing unit 31 waits until the signal T varies from H to L and thereafter repeats the foregoing operations when the signal T alters from H to L again. The resulting data is stored in memories addressed as $M_4$, $M_5$ and $M_6$. In this way, the operations are repeated for the paper pieces 4, 3a, 3b, 3c, . . . for the accumulation of data. On completion of all the measurements, the data processing unit 31 gives the corrected reflectivities of the color reaction test paper pieces 3a, 3b, 3c, . . . based on the data stored in $M_1$, $M_2$, $M_3$, . . .

Methods of determining corrected reflectivities are divided into two in accordance with the characteristics of the color reaction test paper pieces 3a, 3b, 3c, . . .

Figure 8:
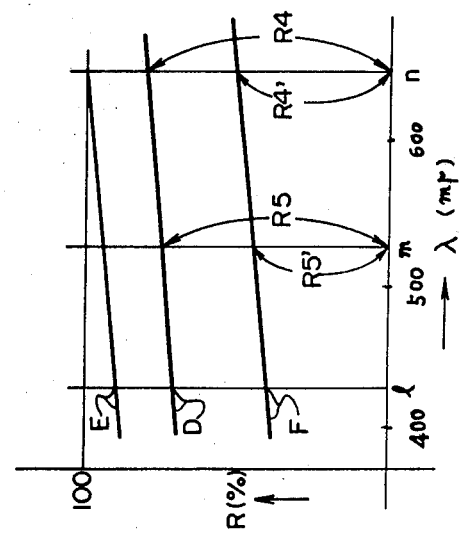

One method is employed in the case where the amount of light reflected from the color reaction test paper piece varies greatly over a wide range of wavelengths owing to variations in the concentration of abnormal substance as shown in FIG. 8, in which Curves D, E and F represent variations in reflectivity at varying concentrations of abnormal substance. According to this method, the data of the amount of light reflected from each of the paper piece 3a, 3b, 3c, . . . is divided by the data of the amount of light reflected from the correcting paper piece 4, and the resulting quotient is taken as the corrected reflectivity of the paper piece concerned. Supposing that the data of the amount of light reflected from the correcting paper piece 4 is $R_{4l}$, $R_{4m}$ and $R_{4n}$ and that the data of the amount of light reflected from the color reaction test paper piece 3a is $R_{3al}$, $R_{3am}$ and $R_{3an}$, the corrected reflectivity of the paper piece 3a at a wavelength of l is $R_{3al}/R_{4l}$, that at a wavelength m is $R_{3am}/R_{4m}$ and that at a wavelength n is $R_{3an}/R_{4n}$. The lowest of these corrected reflectivities (i.e. $R_{3al}/R_{4l}$ in the illustrated case) is processed with a preset conversion factor to indicate the concentration of abnormal substance on a printer 40.

Thus as will be apparent from the drawing, the concentration, even if low, can be accurately determined at a wavelength which produces a marked variation in the amount of reflected light. Because the reflectivity characteristics vary from paper to paper, an optimum measuring wavelength for each paper is detected or determined by the above method for the accurate measurement of the concentration of abnormal substance. In this case, the reflectivity is given in terms of a corrected value free of the influence which would otherwise be produced by the color of the urine sample.

Figure 9:
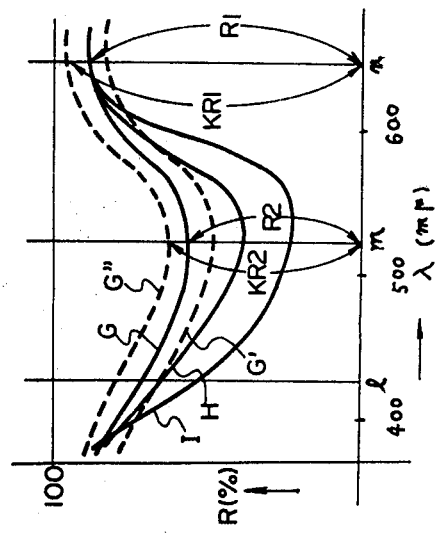
FIGS. 8 and 9 are diagrams showing curves representing different spectral reflectivity characteristics of color reaction test paper pieces.

The other method is used in the case where the amount of reflected light varies greatly with variations in the concentration of abnormal substance only at a specific wavelength as seen in FIG. 9, in which Curves G, H and I represent variations in reflectivity at varying concentration of abnormal substance. In practice, color reaction test paper pieces 3 not infrequently exhibit such reflectivity characteristics. According to the second method, of the corrected (relative) reflectivities obtained by the first method, the reflectivity at a wavelength (m in the drawing) giving a great variation in the amount of reflected light is divided by the reflectivity at a wavelength (n in the drawing) resulting in a small variation, and the resulting quotient is taken as the corrected reflectivity of the paper piece concerned.

This method will be practiced for example for the color reaction test paper piece 3b in the following manner. As in the above description, it is assumed that the relative reflectivity at a wavelength m giving a great variation in the amount of reflected light is $R_{3bm}/R_{4m}$ and that the reflectivity at a wavelength n giving a small variation is $R_{3bn}/R_{4n}$. The corrected reflectivity of the test paper piece 3b will then be expressed as $R_{3bm} \cdot R_{4n}/R_{3bn} \cdot R_{4m}$. Based on this value, the concentration of abnormal substance is calculated by the data processing unit 31 and indicated on the printer 40 as in the first method.

In this way, the concentration is accurately determinable with the use of a measuring wavelength appropriate to the test paper piece 3. Additionally this method can eliminate the measuring errors resulting from variations in the thickness of the paper pieces 4, 3a, 3b, 3c, . . .

Figure 11:
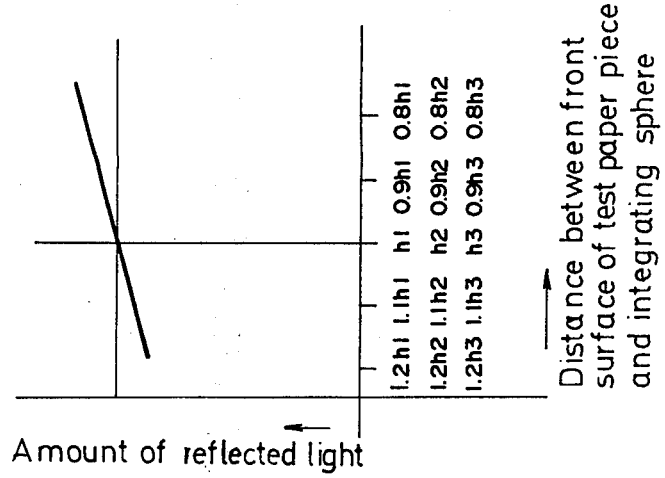
FIG. 11 is a diagram showing the relationship between the amount of reflected light and the distance from the front surfaces of paper pieces to the integrating sphere.
Figure 10:
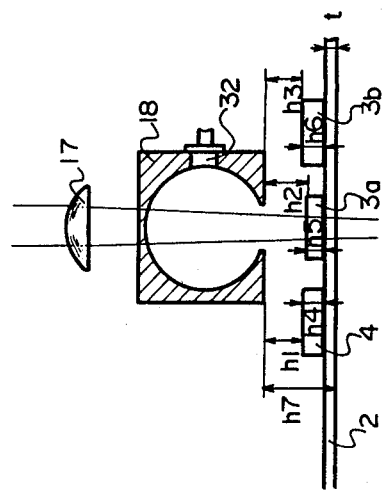
FIG. 10 is a diagram illustrating the relationship between the thicknesses of paper pieces and the distance from the pieces to an integrating sphere.

As seen in FIG. 10, the paper pieces 4, 3a and 3b have thicknesses $h_4$, $h_5$ and $h_6$ which are not always constant owing to variations in the thickness of the filter paper material or to variations in the content of the color reaction reagent. Since the thickness t of the strip 2 as well as the distance $h_7$ from the rear face of the strip 2 to the bottom face of the integrating sphere 18 is definite, this means that the distances $h_1$, $h_2$ and $h_3$ from the front faces of the pieces 4, 3a and 3b to the integrating sphere 18 vary respectively. FIG. 11 shows that the conventional method of measurement at a single wavelength will involve errors.

FIG. 11 showing the rate at which the amount of reflected light varies with $h_1$, $h_2$ and $h_3$ indicates that the amount of light, like the reflectivity, increases as the front surfaces of paper pieces 4, 3a and 3 b approach the integrating sphere 18. Curves G' and G" drawn in dot lines in FIG. 9 represent the data obtained when the same urine sample as in the case of Curve G was tested with use of a color reaction test paper piece of greater thickness and a color reaction test paper piece of smaller thickness than in the case of Curve G. The same paper piece was used for the correction of reflectivity.

The illustrated results indicate that the apparent reflectivity vary greatly in the same ratio at each wavelength, with the thickness of the paper piece. The second method, however, can eliminate the measuring errors due to variations in thickness for the following reason.

Suppose the reflectivity of Curve G in FIG. 9 is $R_2$ at a wavelength m and $R_1$ at a wavelength n. The reflectivity of Curve G" is then $KR_2$ at the wavelength m and $KR_1$ at the wavelength n in which K is a multiple of reflectivity due to a difference in the thickness, namely the distance between the paper surface to the integrating sphere. Accordingly the ratio of the reflectivity at the wavelength m to that at the wavelength n is $R_2/R_1$ in respect of each of Curves G and G''. Thus reflectivity data can be obtained free of the influence of the thickness. However when the color reaction test paper piece has the reflectivity characteristics as illustrated in FIG. 8, the reflectivity ratio between two wavelengths, if taken, will not give the variation of reflectivity due to a variation in concentration ($R_5/R_4$ being approximately equal to $R_5'/R_4'$). It is therefore impossible to use the second method to compensate for the variation in thickness in the occasion as illustrated in FIG. 8.

Figure 12:
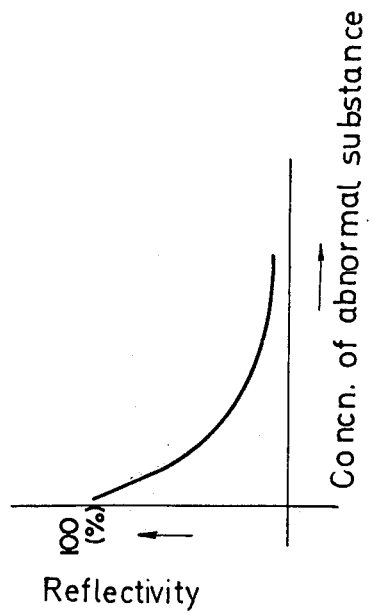
FIG. 12 is a diagram showing a curve representing the relationship between the reflectivity and the concentration of abnormal substance.

FIG. 12 shows the relationship between the reflectivity and the concentration of abnormal substance as determined on a color reaction test paper piece by either one of the above methods. With such relationship stored in the data processing unit 31 for various abnormal substances, the concentrations thereof can be determined immediately from the reflectivities of the paper pieces.

Since the spectral reflectivity of a composite test paper to which a urine or like liquid sample is applied is measured at two or more wavelengths as described above, the reflectivity of each paper piece can be measured at a wavelength at which the amount of reflected light varies greatly. With the use of a reflectivity reference or compensation paper piece, the measurement of the reflectivity as well as the quantitative analysis of an abnormal substance in the sample can be carried out accurately, continuously and rapidly. In the case of color reaction test paper piece involving a great variation in the amount of reflected light at a specific wavelength and a small variation at another specific wavelength, even the measuring errors resulting from variations in the thickness of the paper piece can be eliminated to ensure improved accuracy of the measurement.

What is claimed is:

1. A method of analyzing a liquid sample comprising the steps of applying the sample to a composite test medium formed of a strip having thereon a reflectivity reference piece and at least one color reaction test piece feeding the test medium to spectral reflectivity measuring means, irradiating each of the pieces with energy of a plurality of predetermined different wavelengths, and obtaining corrected reflectivities of each of the test pieces as the relative values with respect to the reflectivity of said reflectivity reference piece from the amounts of reflected energy at at least some of the different wavelengths to measure the concentration of an abnormal substance contained in the test sample.

2. A method of analyzing a liquid sample as in claim 1 wherein the corrected reflectivities are obtained as the relative values of the reflectivities of a test piece at the different wavelengths based on the reflectivities, calculated as 100%, of the reference piece at the corresponding wavelengths, and the concentration of the abnormal substance is measured by the corrected reflectivities at selected wavelengths of the different wavelengths.

3. A method of analyzing a liquid sample as in claim 1 wherein among the relative values of the reflectivities of a test piece at the different wavelengths based on the reflectivities, calculated as 100%, of the reference piece at the corresponding wavelengths, the relative value at one of the wavelengths giving a large variation in the amount of reflected energy is divided by the relative value at another wavelength giving a small variation in the amount of reflected energy, the corrected reflectivity being expressed in terms of the resulting quotient.

4. A system for continuously automatically analyzing liquid samples comprising a sample holder for successively receiving sheets of composite test media in a first position, means for intermittently moving said sample holder, reflectivity measuring means, wavelength selector means disposed adjacent the sample holder for directing energy of several predetermined and different wavelengths through said reflectivity measuring means to irradiate the test media with the energy of selected wavelengths, scanning means disposed adjacent the sample holder and operative while the holder is stopped for moving a test media relative to said selector means, detector means for receiving the output of said reflectivity measuring means, energy transmitted through said test media and energy produced by said wavelength selector means, and a data processing means operative in response to signals from said detector means for determining the reflectivity of the test media.

5. A system for continuously automatically analyzing liquid samples as in claim 4 wherein the wavelength selector means comprises a light source, filter folder means, means for rotating said filter holder means at a constant speed, and a plurality of filters held by said filter holder means and equidistantly spaced apart for passing light rays of predetermined wavelengths, the filters being positionable concentrically with the optical axis of the light, and wavelength identifying signal generator means for such wavelength selector means.

6. A system for continuously automatically analyzing a liquid sample as in claim 5 wherein the wavelength identifying signal generator means comprises apertures formed in the filter holder means and positioned outward of the filters fitted in the holder means, said light source means and light detectors positionable respectively above and below the apertures when the center of the filters is in alignment with the optical axis of the light source means.

7. A system for continuously automatically analyzing a liquid sample as in claim 4 wherein the reflectivity measuring means comprises an integrating sphere and the light detector means therefore is mounted on the integrating sphere.

8. A method as in claim 2 wherein the concentration of the abnormal substance is measured by the corrected reflectivities of all of the different wavelengths.

9. A method of analyzing a liquid sample comprising the steps of:
   applying the sample to at least one color reaction test piece,
   irradiating the test piece with sample applied thereto to a plurality of predetermined different wavelengths of energy,
   and measuring the spectral reflectance of the energy reflected from the test piece at each of said predetermined different wavelengths.

10. A method as in claim 9 further comprising the steps of:
   providing a reflective reference piece,
   irradiating said reflective reference piece with said plurality of different wavelengths of energy and measuring the spectral reflectance therefrom at each of said predetermined different wavelengths, and
   obtaining a corrected spectral reflectance for the test piece from the measurements of the spectral reflectance of both the test piece and the reflective reference piece.

11. A method as in claim 9 wherein the irradiation step is carried out by sequentially irradiating the test piece with the different wavelengths of energy.

12. A method as in claim 10 wherein the irradiation step is carried out by sequentially irradiating the test piece and the reflective reference piece with the different wavelengths of energy.

13. A system for analyzing for different substances in a liquid sample which has been applied to a test piece comprising:

means for irradiating the test piece with light energy of a plurality of different, predetermined wavelengths, means for measuring the reflectance of the light from the test piece of at least a selected plurality of the different wavelengths, and means responsive to the measured values of reflected light for analyzing for the substance.

14. A system as in claim 13 wherein said test piece is located on a carrier, said carrier further including a reference piece of a given reflectivity, said irradiating means irradiating both said test piece and said reference piece with light energy of a plurality of different predetermined wavelengths, said measuring means being responsive to the light reflected from both said test piece and said reference piece for producing corrected relative values of the amount of light reflected at a plurality of the selected wavelengths.

15. A system as in claim 14 wherein said carrier for the pieces comprises a strip and said irradiating means comprises a fixed position light source, and means for moving the strip relative to the light source.

16. A system as in claim 15 wherein said irradiating means also includes a plurality of filter means each defining one of said plurality of wavelengths, and means for moving said filter means relative to said light source.

* * * * *